United States Patent
Jung et al.

(10) Patent No.: US 9,487,833 B2
(45) Date of Patent: Nov. 8, 2016

(54) **PRIMER SET SPECIFIC FOR VANCOMYCIN-RESISTANT *ENTEROCOCCUS*, COMPOSITION COMPRISING THE SAME AND METHOD OF DETECTING VANCOMYCIN-RESISTANT MICROORGANISM *ENTEROCOCCUS* IN SAMPLE**

(71) Applicant: Samsung Electronics Co., Ltd., Suwon-si, Gyeonggi-do (KR)

(72) Inventors: Sunok Jung, Seongnam-si (KR); Joonho Kim, Seongnam-si (KR); Kyuyoun Hwang, Seoul (KR); Sookwan Lee, Seoul (KR); Seahee Kim, Seoul (KR); Kobong Choi, Osan-si (KR)

(73) Assignee: SAMSUNG ELECTRONICS CO., LTD, Suwon-Si (KR)

( * ) Notice: Subject to any disclaimer, the term of this patent is extended or adjusted under 35 U.S.C. 154(b) by 143 days.

(21) Appl. No.: 14/486,617

(22) Filed: Sep. 15, 2014

(65) Prior Publication Data

US 2015/0252410 A1    Sep. 10, 2015

(30) Foreign Application Priority Data

Mar. 6, 2014    (KR) .................. 10-2014-0026818

(51) Int. Cl.
*C12Q 1/68*    (2006.01)
(52) U.S. Cl.
CPC ......... *C12Q 1/689* (2013.01); *C12Q 2600/158* (2013.01)
(58) Field of Classification Search
None
See application file for complete search history.

(56) References Cited

U.S. PATENT DOCUMENTS

| | | | |
|---|---|---|---|
| 5,234,809 A | 8/1993 | Boom et al. | |
| 5,776,563 A | 7/1998 | Buhl et al. | |
| 5,804,375 A | 9/1998 | Gelfand et al. | |
| 5,958,349 A | 9/1999 | Petersen et al. | |
| 6,156,507 A | 12/2000 | Hiramatsu et al. | |
| 6,303,305 B1 | 10/2001 | Wittwer et al. | |
| 6,358,679 B1 | 3/2002 | Heid et al. | |
| 6,369,893 B1 | 4/2002 | Christel et al. | |
| 6,431,476 B1 | 8/2002 | Taylor et al. | |
| 6,432,290 B1 | 8/2002 | Harrison et al. | |
| 6,503,720 B2 | 1/2003 | Wittwer et al. | |
| 6,691,041 B2 | 2/2004 | Sagner et al. | |
| 6,814,934 B1 | 11/2004 | Higuchi | |
| 6,887,693 B2 | 5/2005 | McMillan et al. | |
| 6,914,137 B2 | 7/2005 | Baker | |
| 7,312,611 B1 | 12/2007 | Harrison et al. | |
| 7,439,023 B2 | 10/2008 | Hwang et al. | |
| 7,445,926 B2 | 11/2008 | Mathies et al. | |
| 7,838,300 B2 | 11/2010 | Namkoong et al. | |
| 7,923,551 B2 | 4/2011 | Lee et al. | |
| 8,017,337 B2 | 9/2011 | Paitan | |
| 8,185,324 B2 | 5/2012 | Namkoong et al. | |
| 8,580,506 B2 | 11/2013 | Jung et al. | |
| 2005/0058985 A1 | 3/2005 | Dodgson | |
| 2007/0059714 A1* | 3/2007 | Strommenger | ........ C12Q 1/689 435/6.13 |
| 2008/0044884 A1 | 2/2008 | Hwang et al. | |
| 2010/0267012 A1 | 10/2010 | Bergeron et al. | |
| 2011/0200995 A1 | 8/2011 | Reiske et al. | |
| 2011/0286885 A1 | 11/2011 | Park et al. | |
| 2012/0107823 A1 | 5/2012 | Hwang et al. | |
| 2012/0171681 A1 | 7/2012 | Malig et al. | |
| 2012/0280143 A1 | 11/2012 | Kim et al. | |
| 2013/0264205 A1 | 10/2013 | Hwang et al. | |
| 2013/0306160 A1 | 11/2013 | Chung et al. | |

FOREIGN PATENT DOCUMENTS

KR    2011-0115876 A    10/2011

OTHER PUBLICATIONS

Khan et al., Molecular characterization of multidrug-resistant *Enterococcus* spp. from poultry and dairy farms: detection of virulence and vancomycin resistance gene markers by PCR, Mol Cell Probes. Feb. 2005;19(1):27-34. Epub Nov. 12, 2004.*
Patel et al., Multiplex PCR detection of vanA, vanB, vanC-1, and vanC-2/3 genes in enterococci, J Clin Microbiol. Mar. 1997; 35(3): 703-707.*
Boyd et al., Enterococcus gallinarum N04-0414 Harbors a VanD-Type Vancomycin Resistance Operon and Does Not Contain a d-Alanine:d-Alanine 2 (ddl2) Gene, Antimicrob Agents Chemother. Mar. 2006; 50(3): 1067-1070.*
Ambur et al., d-Ala:d-Ala Ligase Gene Flanking the vanC Cluster: Evidence for Presence of Three Ligase Genes in Vancomycin-Resistant Enterococcus gallinarum BM4174, Antimicrob Agents Chemother. Jan. 2002; 46(1): 95-100.*
Andersson et al., "The Paranasal Sinuses as Reservoirs for Nitric Oxide", *Acta Otolaryngol*, 122:861-865 (2002).
Fang, "Anitmicrobial Reactive Oxygen and Nitrogen Species: Concepts and Controversies", *Nature*, 2: 820-832 (2004).
Khan et al.,"Molecular characterization of multidrug-resistant *Enterococcus* spp.from poultry and dairy farms: detection of virulence and vancomycin resistance gene markers by PCR", *Molecular and Cellular Probes*, 19: 27-34 (2005).
McKessar et al., "Genetic Characterization of vanG, a Novel Vancomycin Resistance Locus of *Enterococcus faecalis*", *Antimicrobial Agents and Chemotherapy*, 44(11): 3224-3228 (2000).
Milewski et al. "Overproduction of a 37-kilodalton cytoplasmic protein homologous to NAD+-linked D-lactate dehydrogenase associated with vancomycin resistance in *Staphylococcus aureus.*", *Antimicrob. Agents Chemother.*, 40(1): 166-172 (1996).
Richardson et al., "A Nitric Oxide-Inducible Lactate Dehydrogenase Enables *Staphylococcus aureus* to Resist Innate Immunity", *Science*, 319: 1672-1676 (2008).
Shay et al, "Impairment of Antimicrobial Activity and Nitric Oxide Production in Alveolar Macrophages from Smokers of Marijuana and Cocaine", *Journal of Infectious Diseases*, 187: 700-704 (2003).

* cited by examiner

*Primary Examiner* — Aaron Priest
(74) *Attorney, Agent, or Firm* — Leydig, Voit & Mayer, Ltd.

(57) ABSTRACT

A vancomycin-resistant *Enterococcus* specific primer set, a composition including the primer set, and a method of detecting a vancomycin-resistant *Enterococcus* sp. microorganism in a sample using the primer set.

16 Claims, 4 Drawing Sheets

US 9,487,833 B2

PRIMER SET SPECIFIC FOR VANCOMYCIN-RESISTANT *ENTEROCOCCUS*, COMPOSITION COMPRISING THE SAME AND METHOD OF DETECTING VANCOMYCIN-RESISTANT MICROORGANISM *ENTEROCOCCUS* IN SAMPLE

RELATED APPLICATION

This application claims the benefit of Korean Patent Application No. 10-2014-0026818, filed on Mar. 6, 2014, in the Korean Intellectual Property Office, the entire disclosure of which is hereby incorporated by reference.

INCORPORATION BY REFERENCE OF ELECTRONICALLY SUBMITTED MATERIALS

Incorporated by reference in its entirety herein is a computer-readable nucleotide/amino acid sequence listing submitted herewith and identified as follows: 5,584 bytes ASCII (Text) file named "718061_ST25.TXT," created Sep. 12, 2014.

BACKGROUND

1. Field

The present disclosure relates to a primer set specific for vancomycin-resistant *Enterococcus*, a composition including the primer set, and a method of detecting a vancomycin-resistant *Enterococcus* genus microorganism in a sample.

2. Description of the Related Art

Enterococci are gram-positive cocci that are considered as general habitants in digestive systems and female genital tracts. Enterococci species do not particularly induce diseases in humans, but vancomycin-resistant Enterococci (VRE) are primary pathogenetic bacteria in nosocomial (i.e., hospital-acquired) infections. Recently, nosocomial infections caused by VRE are increasing. Currently, about 30% to about 45% of Enterococci samples taken from intensive care units (*Enterococcus faecalis*) exhibit resistance to vancomycin. As such, a suitable infection management for the VRE is needed.

A conventional method of detection, such as inoculation of Enterococci in a VRE selection solid medium or inoculation of Enterococci in a solid medium after proliferation of the Enterococci in a selection liquid medium, takes about 4 days to about 7 days. Accordingly, a method of precisely detecting VRE at low cost and within a short time is needed.

SUMMARY

Provided is a primer set for detecting vancomycin-resistant Enterococci species selected from the group consisting of *Enterococcus faecalis*, *Enterococcus faecium*, *Enterococcus gallinarum*, and *Enterococcus casseliflavus*.

Also provided is a composition for detecting vancomycin-resistant Enterococci species selected from the group consisting of *Enterococcus faecalis*, *Enterococcus faecium*, *Enterococcus gallinarum*, and *Enterococcus casseliflavus*.

Further provided is a method of detecting one or more Enterococci genus microorganisms having or expressing vancomycin resistance genes.

BRIEF DESCRIPTION OF THE DRAWINGS

These and/or other aspects will become apparent and more readily appreciated from the following description of the embodiments, taken in conjunction with the accompanying drawings in which:

In FIGS. 3 to 6, the vertical axis is a response unit measuring fluorescence emitted from FAM, the horizontal axis is a cycle number, M is a size marker, and each of $10^3$, $10^2$, $10^1$, and $10^0$ represents the specific number of *Enterococcus* for each reaction solution.

DETAILED DESCRIPTION

Figure 1:
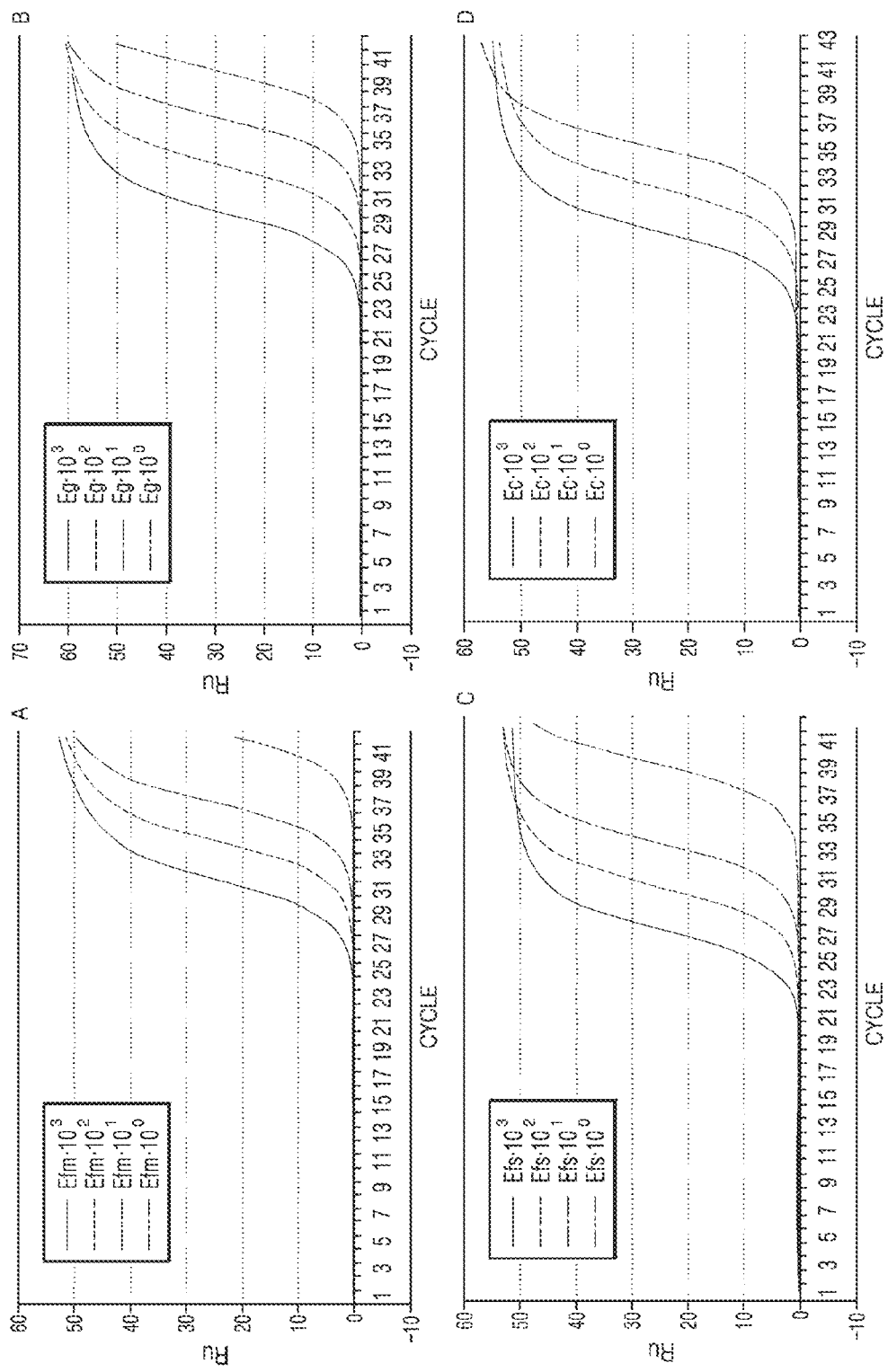
FIG. 1 shows real-time PCR results of single PCR amplification products using primer sets 1 to 4 in curves A-D, respectively.

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects of the present description. As used herein, the term "and/or" includes any and all combinations of one or more of the associated listed items. Expressions such as "at least one of," when preceding a list of elements, modify the entire list of elements and do not modify the individual elements of the list.

According to an aspect of the present disclosure, provided is a primer set for use in detection of a vancomycin-resistant *Enterococcus* species selected from the group consisting of *Enterococcus faecalis*, *Enterococcus faecium*, *Enterococcus gallinarum*, and *Enterococcus casseliflavus*, including at least one primer set, which includes at least one *Enterococcus* sp. specific primer set selected from the group consisting of: a first primer set including a polynucleotide which includes 10 or more contiguous nucleotides selected from a nucleotide sequence of SEQ ID NO: 1 and a polynucleotide that includes 10 or more contiguous nucleotides selected from a nucleotide sequence of SEQ ID NO: 2; a second primer set including a polynucleotide which includes 10 or more contiguous nucleotides selected from a nucleotide sequence of SEQ ID NO: 4 and a polynucleotide that includes 10 or more contiguous nucleotides selected from SEQ ID NO: 5; a third primer set including a polynucleotide which includes 10 or more contiguous nucleotides selected from a nucleotide sequence of SEQ ID NO: 7 and a polynucleotide that includes 10 or more contiguous nucleotides selected from SEQ ID NO: 8; a fourth primer set including a polynucleotide which includes 10 or more contiguous nucleotides selected from a nucleotide sequence of SEQ ID NO: 10 and a polynucleotide that includes 10 or more contiguous nucleotides selected from SEQ ID NO: 11; and at least one vancomycin resistance gene specific primer set selected from the group consisting of: a fifth primer set including a polynucleotide which includes 10 or more contiguous nucleotides selected from a nucleotide sequence of SEQ ID NOs. 13 and a polynucleotide that comprises 10 or more contiguous nucleotides selected from a nucleotide sequence of SEQ ID NO: 14; a sixth primer set including a polynucleotide which includes 10 or more contiguous nucleotides selected from a nucleotide sequence of SEQ ID NO: 16 and a polynucleotide that includes 10 or more contiguous nucleotides selected from SEQ ID NO: 17; a seventh primer set including a polynucleotide which includes 10 or more contiguous nucleotides selected from a nucleotide sequence of SEQ ID NO: 19 and a polynucleotide that includes 10 or more contiguous nucleotides selected from SEQ ID NO: 20; and an eighth primer set including a polynucleotide which includes 10 or more contiguous nucleotides selected from a nucleotide sequence of SEQ ID NO: 22 and a polynucleotide that includes 10 or more contiguous nucleotides selected from SEQ ID NO: 23.

The primer set may include a single primer set or a plurality of primer sets (e.g., sub-sets). The primer set including a plurality of primer sets may include one primer set from the first to the fourth *Enterococcus* sp. specific primer sets and 1 to 4 primer sets from the fifth to the eighth vancomycin resistance gene specific primer sets; two primer sets from the first to the fourth *Enterococcus* sp. specific primer sets and 1 to 4 primer sets from the fifth to the eighth vancomycin resistance gene specific primer sets; three primer sets from the first to the fourth *Enterococcus* sp. specific primer sets and 1 to 4 primer sets from the fifth to the eighth vancomycin resistance gene specific primer sets, or the first to the fourth *Enterococcus* sp. specific primer sets and 1 to 4 primer sets of the fifth to the eighth vancomycin resistance gene specific primer sets.

The primer may have a length of about 10 nts to about 25 nts, about 10 nts to about 24 nts, about 10 nts to about 23 nts, about 10 nts to about 22 nts, about 10 nts to about 21 nts, about 10 nts to about 20 nts, about 10 nts to about 19 nts, about 10 nts to about 18 nts, about 10 nts to about 17 nts, about 10 nts to about 16 nts, about 10 nts to about 15 nts, about 12 nts to about 25 nts, about 12 nts to about 24 nts, about 12 nts to about 23 nts, about 12 nts to about 22 nts, about 12 nts to about 21 nts, about 12 nts to about 20 nts, about 12 nts to about 19 nts, about 12 nts to about 18 nts, about 12 nts to about 17 nts, about 12 nts to about 16 nts, about 12 nts to about 15 nts, about 14 nts to about 25 nts, about 14 nts to about 24 nts, about 14 nts to about 23 nts, about 14 nts to about 22 nts, about 14 nts to about 21 nts, about 14 nts to about 20 nts, about 14 nts to about 19 nts, about 14 nts to about 18 nts, about 14 nts to about 17 nts, about 14 nts to about 16 nts, about 14 nts to about 15 nts, about 15 nts to about 25 nts, about 15 nts to about 20 nts, about 15 nts to about 17 nts, about 17 nts to about 25 nts, about 17 nts to about 23 nts, or about 17 nts to about 20 nts.

In the primer set, the first primer set, second primer set, third primer set, fourth primer set, fifth primer set, sixth primer set, seventh primer set, and eighth primer set may be used for specific amplification of an *Enterococcus faecalis* lactate dehydrogenase gene (ldh), an *Enterococcus faecium* lactate dehydrogenase gene (ldh), *Enterococcus gallinarum* D-alanine: D-alanine ligase gene2 (ddl2), and an *Enterococcus casseliflavus* lactate dehydrogenase gene (ldh), a VanA gene, a VanB gene, a VanC1 gene, and a VanC2/3 gene, respectively.

The primer may be attached to a detectable label. The detectable label may be an optical label, an electrical label, a radioactive label, an enzymatic label, or a combination thereof. The optical label may be a material that generates fluorescence or phosphorescence. A phosphorescent material may be, for example, fluorescein, rhodamine, cyanine, a metal porphyrin complex, Cy-5, and Cy-3. Examples of a fluorescein dye include 6-carboxyl fluorescein (6-FAM) 1,2',4',1,4,-tetrachloro-fluorescein (TET) 2, and 2',4',5',7',1,4-hexachloro-fluorescein (HEX) 3,2',7'-dimethoxy-4',5'-dichloro-6-carboxyrhodamine (JOE) 4,2'-chloro-5'-fluoro-7',8'-fused phenyl-1,4-dichloro-6-carboxy-fluoroscein 5, and 2'-chloro-7'-phenyl-1,4-dichloro-6-carboxy-fluoroscein 6.

The primer set may further include a polynucleotide probe specific to at least one of target genes, such as an *Enterococcus faecalis* lactate dehydrogenase gene (ldh), an *Enterococcus faecium* lactate dehydrogenase gene (ldh), an *Enterococcus gallinarum* D-alanine: D-alanine ligase gene2 (ddl2), and an *Enterococcus casseliflavus* lactate dehydrogenase gene (ldh), a VanA gene, a VanB gene, a VanC1 gene, and a VanC2/3 gene.

The primer set may further include at least one probe specific for *Enterococcus* sp. specific gene selected from the group consisting of: a first probe including 10 or more contiguous nucleotides selected from a nucleotide sequence of SEQ ID NO: 3; a second probe including 10 or more contiguous nucleotides selected from a nucleotide sequence of SEQ ID NO: 6; a third probe including 10 or more contiguous nucleotides selected from a nucleotide sequence of SEQ ID NO: 9; and a fourth probe including 10 or more contiguous nucleotides selected from a nucleotide sequence of SEQ ID NO: 12; and at least one probe specific for vancomycin resistance gene selected from the group consisting of: a fifth probe including 10 or more contiguous nucleotides selected from a nucleotide sequence of SEQ ID NO: 15; a sixth probe including 10 or more contiguous nucleotides selected from a nucleotide sequence of SEQ ID NO: 18; a seventh probe including 10 or more contiguous nucleotides selected from a nucleotide sequence of SEQ ID NO: 21; and an eighth probe including 10 or more contiguous nucleotides selected from a nucleotide sequence of SEQ ID NO: 24. The first probe, the second probe, the third probe, the fourth probe, the fifth probe, the sixth probe, the seventh probe, and the eighth probe may be used for specific detection of an *Enterococcus faecalis* lactate dehydrogenase gene (ldh), an *Enterococcus faecium* lactate dehydrogenase gene (ldh), an *Enterococcus gallinarum* D-alanine: D-alanine ligase gene (ddl2), and an *Enterococcus casseliflavus* lactate dehydrogenase gene (ldh), a VanA gene, a VanB gene, a VanC1 gene, and a VanC2/3 gene.

The *Enterococcus faecalis* lactate dehydrogenase gene (ldh) may have a nucleotide sequence of gi29374661 or gi307638684; the *Enterococcus faecium* lactate dehydrogenase gene (ldh) may have a nucleotide sequence of gi484100370, gi389867183, or gi388532432; the *Enterococcus gallinarum* D-alanine: D-alanine ligase gene (ddl2) may have a nucleotide sequence of gi62632242, gi62632240, or gi1244571; and the *Enterococcus casseliflavus* lactate dehydrogenase gene (ldh) may have a nucleotide sequence of gi482850047 or gi325573643. The VanA gene, VanB gene, VanC1 gene, and VanC2/3 gene may belong to an *Enterococcus* genus.

The probe may be attached to a detectable label. The detectable label may be an optical label, an electrical label, a radioactive label, an enzymatic label, or a combination thereof. The optical label may be a material that generates fluorescence or phosphorescence. A phosphorescent material may be, for example, fluorescein, rhodamine, cyanine, a metal porphyrin complex, Cy-5, and Cy-3. Examples of a fluorescein dye include 6-carboxyl fluorescein (6-FAM) 1,2',4',1,4,-tetrachloro-fluorescein (TET) 2, and 2',4',5',7',1, 4-hexachloro-fluorescein (HEX) 3,2',7'-dimethoxy-4',5'-dichloro-6-carboxyrhodamine (JOE) 4,2'-chloro-5'-fluoro-7', 8'-fused phenyl-1,4-dichloro-6-carboxy-fluoroscein 5, and 2'-chloro-7'-phenyl-1,4-dichloro-6-carboxy-fluoroscein 6. The probe may be labeled by a detectable label that may be used in a real-time polymerase chain reaction (PCR). The detectable label that may be used in a real-time PCR may be a FRET pair. The probe may be a TaqMan™ probe.

The probe may have a length of about 10 nts to about 25 nts, about 10 nts to about 24 nts, about 10 nts to about 23 nts, about 10 nts to about 22 nts, about 10 nts to about 21 nts, about 10 nts to about 20 nts, about 10 nts to about 19 nts, about 10 nts to about 18 nts, about 10 nts to about 17 nts, about 10 nts to about 16 nts, about 10 nts to about 15 nts, about 12 nts to about 25 nts, about 12 nts to about 24 nts, about 12 nts to about 23 nts, about 12 nts to about 22 nts, about 12 nts to about 21 nts, about 12 nts to about 20 nts, about 12 nts to about 19 nts, about 12 nts to about 18 nts, about 12 nts to about 17 nts, about 12 nts to about 16 nts, about 12 nts to about 15 nts, about 14 nts to about 25 nts, about 14 nts to about 24 nts, about 14 nts to about 23 nts, about 14 nts to about 22 nts, about 14 nts to about 21 nts, about 14 nts to about 20 nts, about 14 nts to about 19 nts, about 14 nts to about 18 nts, about 14 nts to about 17 nts, about 14 nts to about 16 nts, about 14 nts to about 15 nts, about 15 nts to about 25 nts, about 15 nts to about 20 nts, about 15 nts to about 17 nts, about 17 nts to about 25 nts, about 17 nts to about 23 nts, or about 17 nts to about 20 nts.

By using the primer set in a multiplex PCR, a microorganism and an *Enterococcus* sp. having vancomycin resistance in a sample may be simultaneously identified and detected. Also, the primer set may be simultaneously used in a plurality of single PCRs to simultaneously identify and detect a microorganism and an *Enterococcus* sp. having vancomycin resistance in a sample.

With regards to the primer set, the detection may occur through amplification of a target nucleic acid by using the primer set and detection of the amplification products obtained therefrom. The amplification may occur through a PCR, a ligase chain reaction (LCR), and a strand displacement amplification (SDA), which includes repetitions of hybridization of a primer with a target nucleic acid sequence and elongation of a hybridized primer obtained therefrom. The acronym "PCR" as used herein refers to a polymerase chain reaction, which is a method of amplifying a target nucleic acid by using a primer set that specifically binds to the target nucleic acid by using a polymerase. The PCR method is well known in the art, which may be performed by using a commercially available kit. The PCR method includes a single PCR which amplifies a single target at a time and a multiplex PCR which amplifies a plurality of targets at a time. A plurality of primer sets are used in the multiplex PCR. The detection may be a simultaneous detection of at least one *Enterococcus* sp. and vancomycin resistance thereof.

According to another aspect of the present disclosure, provided is a composition including a primer set for detection of the vancomycin-resistant *Enterococcus* sp. described above, the composition for use in detection of a vancomycin-resistant *Enterococcus* sp. selected from the group consisting of *Enterococcus faecalis*, *Enterococcus faecium*, *Enterococcus gallinarum*, and *Enterococcus casseliflavus*.

With regards to the composition, the primer set for detection of the vancomycin-resistant *Enterococcus* sp. is as described above. The composition may be a liquid or a solid composition. The composition may further include a reagent or a compound used in a nucleic acid amplification reaction. The composition may include water, solvent, buffer, salt, nucleic acid from a control group, coenzyme, dNTP, DNA polymerase, or a combination thereof. When a probe is included in the composition, the probe may be immobilized on a substrate. The composition may further include one or more target nucleic acids to be detected, e.g., a target nucleic acid to which the primers specific to *Enterococcus* hybridize and/or a target nucleic acid to which the primers specific to vancomycin resistance bind.

According to another aspect of the present disclosure, provided is a kit including a primer set for use in the detection of vancomycin-resistant *Enterococcus* sp. selected from the group consisting of *Enterococcus faecalis*, *Enterococcus faecium*, *Enterococcus gallinarum*, and *Enterococcus casseliflavus*.

With regards to the kit, the primer set for use in a simultaneous use in a multiplex PCR for the detection of a vancomycin-resistant *Enterococcus* sp. may be as described above. The kit may further include a reagent or a compound used in a nucleic acid amplification reaction. The kit may include water, solvent, salt, control group nucleic acid, buffer, coenzyme, dNTP, DNA polymerase, a manual protocol, or a combination thereof. When the kit includes probes, the probes may be immobilized to a substrate. The substrate may be a microarray.

According to another aspect of the present disclosure, provided is a method of detecting at least one *Enterococcus* genus microorganism expressing a vancomycin resistance gene, the method including:

providing a primer set specific for at least one *Enterococcus* sp., the primer set including a polynucleotide which includes 10 or more contiguous nucleotides selected from a nucleotide sequence of SEQ ID NO: 1 and a polynucleotide that includes 10 or more contiguous nucleotides selected from a nucleotide sequence of SEQ ID NO: 2; a second primer set including a polynucleotide which includes 10 or more contiguous nucleotides selected from a nucleotide sequence of SEQ ID NO: 4 and a polynucleotide that includes 10 or more contiguous nucleotides selected from SEQ ID NO: 5; a third primer set including a polynucleotide which includes 10 or more contiguous nucleotides selected from a nucleotide sequence of SEQ ID NO: 7 and a polynucleotide that includes 10 or more contiguous nucleotides selected from SEQ ID NO: 8; and a fourth primer set including a polynucleotide which includes 10 or more contiguous nucleotides selected from a nucleotide sequence of SEQ ID NO: 10 and a polynucleotide that includes 10 or more contiguous nucleotides selected from SEQ ID NO: 11;

providing at least one primer set specific for a vancomycin resistance gene selected from a fifth primer set including a polynucleotide which includes 10 or more contiguous nucleotides selected from a nucleotide sequence of SEQ ID NOs. 13 and a polynucleotide that includes 10 or more contiguous nucleotides selected from a nucleotide sequence of SEQ ID NO: 14; a sixth primer set including a polynucleotide which includes 10 or more contiguous nucleotides selected from a nucleotide sequence of SEQ ID NO: 16 and a polynucleotide that includes 10 or more contiguous nucleotides selected from SEQ ID NO: 17; a seventh primer set including a polynucleotide which includes 10 or more contiguous nucleotides selected from a nucleotide sequence of SEQ ID NO: 19 and a polynucleotide that includes 10 or more contiguous nucleotides selected from SEQ ID NO: 20; and an eighth primer set including a polynucleotide which includes 10 or more contiguous nucleotides selected from a nucleotide sequence of SEQ ID NO: 22 and a polynucleotide that includes 10 or more contiguous nucleotides selected from SEQ ID NO: 23;

contacting the primer set specific for at least one *Enterococcus* genus and/or a primer set specific for at least one vancomycin resistance gene with a sample that is suspected to include at least one *Enterococcus* sp. microorganism expressing or including a vancomycin resistance gene to hybridize a target nucleic acid to the primer set, wherein the target nucleic acid is at least one from an *Enterococcus faecalis* lactate dehydrogenase gene (ldh), an *Enterococcus faecium* lactate dehydrogenase gene (ldh), *Enterococcus galinarum* D-alanine: D-alanine ligase gene2 (ddl2), an *Enterococcus casseliflavus* lactate dehydrogenase gene (ldh), a VanA gene, a VanB gene, a VanC1 gene, and a VanC2/3 gene;

elongating the primer in a hybridization product obtained therefrom to amplify the target nucleic acid; and identifying the presence of the target nucleic acid in an amplification product obtained therefrom.

The method includes providing a primer set specific for at least one *Enterococcus* sp. and a primer set specific for at least one vancomycin resistance gene. The primer set specific for at least one *Enterococcus* sp. and the primer set specific for at least one vancomycin resistance gene may be the same as those described for the primer set for use in the detection of a vancomycin-resistant *Enterococcus* sp.

The method also includes contacting the primer set specific for at least one *Enterococcus* and/or a primer set specific for at least one vancomycin resistance gene with a sample that is suspected to include at least one *Enterococcus* sp. microorganism expressing or including a vancomycin resistance gene to hybridize a target nucleic acid to the primer set, wherein the target nucleic acid is at least one from an *Enterococcus faecalis* lactate dehydrogenase gene (ldh), an *Enterococcus faecium* lactate dehydrogenase gene (ldh), *Enterococcus gallinarum* D-alanine: D-alanine ligase gene2 (ddl2), an *Enterococcus casseliflavus* lactate dehydrogenase gene (ldh), a VanA gene, a VanB gene, a VanC1 gene, and a VanC2/3 gene.

The contact may occur through an incubation of the sample and the primer set in a liquid medium. The incubation may occur through agitation or without agitation. The liquid medium may be water, buffer, or a combination thereof. The liquid medium may be a PCR reagent mixture including a PCR reagent. The incubation may occur at a suitable temperature for hybridization. A temperature for the hybridization may be about 4° C. to about 65° C., for example, about 50° C. to about 65° C., about 55° C. to about 65° C., or about 60° C. to about 65° C. The contact may correspond to annealing in PCR.

The sample may be a biological material. The biological material may be a fresh or stored sample of an organ or tissue, or a solid tissue such as a biopsy; blood or blood components; bodily fluid such as amniotic fluid, peritoneal fluid, or interstitial fluid; cells; or a combination thereof. The sample may include material such as preservatives, anticoagulants, buffers, fixatives, and nutrients, and compounds that are not naturally found in the sample. A biological sample may be, for example, urine, mucus, saliva, tears, blood, plasma, serum, sputum, spinal fluid, pleural fluid, nipple aspirates, lymph, respiratory tract fluid, serous, urogenital canal fluid, breast milk, lymphatic fluid, semen, cerebrospinal fluid, body fluid of an organ system, ascites, cystic tumor fluid, amniotic fluid, rectal swap, or a combination thereof. The sample may be collected from a surface of an inanimate object such as a medical device. The sample may already have been separated from the individual. The method may be an ex vivo or an in vivo method.

During the process, the presence of an amplification product of the first primer set indicates that *Enterococcus faecalis* exists in the sample, the presence of an amplification product of the second primer set indicates that *Enterococcus faecium* exists in the sample, the presence of an amplification product of the third primer set indicates that *Enterococcus gallinarum* exists in the sample, the presence of an amplification product of the fourth primer set indicates that *Enterococcus casseliflavus* exists in the sample, the presence of an amplification product of the fifth primer set indicates that VanA resistant microorganisms exists in the sample, the presence of an amplification product of the sixth primer set indicates that VanB resistant microorganism exists in the sample, the presence of an amplification product of the seventh primer set indicates that a VanC1 resistant microorganism exists in the sample, and the presence of an amplification product of the eighth primer set indicates that a VanC2/3 resistant microorganism exists in the sample. Accordingly, the type of the microorganism in the sample may be identified and vancomycin resistance thereof may be detected simultaneously.

The method includes elongating the primer in the hybridization product obtained therefrom to amplify the target nucleic acid.

The amplification may occur through a PCR, an LCR, and an SDA, which includes repetitions of hybridization of a primer to a nucleic acid sequence and elongation of a hybridized primer obtained therefrom. The acronym "PCR" as used herein refers to a polymerase chain reaction, which is a method of amplifying a target nucleic acid by using a primer set) that specifically binds to the target nucleic acid by using a polymerase. The PCR method is well known in the art, which may be performed by using a commercially available kit. The PCR method includes a single PCR, which amplifies a single target at a time, and a multiplex PCR, which amplifies a plurality of targets at a time. A plurality of primer sets are used in the multiplex PCR. The detection may be a simultaneous detection of at least one *Enterococcus* sp. and vancomycin resistance thereof. Also, the PCR may be real-time PCR (RT-PCR) or quantitative real-time PCR (qRT-PCR).

The method includes identifying the presence of the target nucleic acid among the amplification products. The identifying may include separation and detection of the amplification products. The separation may occur through electrophoresis, hybridization, or a combination thereof. The detection may include binding the target nucleic acid to a probe that specifically binds to the target nucleic acid and then detecting a signal therefrom. Identifying the presence of the target nucleic acid among the amplification products may further include hybridization of the amplification product to a probe specific for the amplification product. The hybridization product may be detected to identify the presence of the target nucleic acid.

The probe may further include at least one of a first probe including 10 or more contiguous nucleotides selected from a nucleotide sequence of SEQ ID NO: 3; a second probe including 10 or more contiguous nucleotides selected from a nucleotide sequence of SEQ ID NO: 6; a third probe including 10 or more contiguous nucleotides selected from a nucleotide sequence of SEQ ID NO: 9; and a fourth probe including 10 or more contiguous nucleotides selected from a nucleotide sequence of SEQ ID NO: 12; a fifth probe including 10 or more contiguous nucleotides selected from a nucleotide sequence of SEQ ID NO: 15; a sixth probe including 10 or more contiguous nucleotides selected from a nucleotide sequence of SEQ ID NO: 18; a seventh probe including 10 or more contiguous nucleotides selected from a nucleotide sequence of SEQ ID NO: 21; and an eighth probe including 10 or more contiguous nucleotides selected from a nucleotide sequence of SEQ ID NO: 24. The probe is as described herein.

The method may further include separating nucleic acid from a sample and enriching an *Enterococcus* sp. microorganism before the separating the nucleic acid. Separating the nucleic acid may be performed before the contact. The enrichment may be performed in a medium that may selectively allow the proliferation of the *Enterococcus* sp. microorganism. The separation and the enrichment of the nucleic acid may occur through a method known in the art.

The method may further include separation of a sample from an individual. The individual may be an animal, for example, a mammal. The mammal may be a human, dog, pig, cow, horse, goat, sheep, or cat. The separation may include extraction of tissue that is suspected to be infected by *Enterococcus* sp. bacteria, for example, infected tissue or wound. The method may be an in vitro method performed on the separated sample.

The primer set for use in the detection of a vancomycin-resistant *Enterococcus* sp. according to an aspect of the present disclosure may be used for efficient detection of a vancomycin-resistant *Enterococcus* in a sample.

The composition or the kit for use in the detection of a vancomycin-resistant *Enterococcus* sp. according to another aspect of the present disclosure may be used for efficiently detecting the vancomycin-resistant *Enterococcus* sp. in the sample.

The method of detecting at least one *Enterococcus* sp. specific microorganism expressing a vancomycin resistance gene, according to another aspect of the present disclosure, may be used to efficiently detect at least one *Enterococcus* sp. microorganism expressing the vancomycin resistance gene.

Hereinafter, the present disclosure will be described in greater detail through embodiments. However, the embodiments are for illustrative purposes only and the scope of the present disclosure is not limited to the embodiments.

Example 1

Design of a Primer Set for Detecting Four Vancomycin Resistance Genes and Four *Enterococcus* Species (1) Design and Confirmation of Properties of a Primer Set for Detecting Four *Enterococcus* Species First, primer sets suitable for specifically detecting each of four *Enterococcus* species, *Enterococcus faecalis* (hereinafter, also referred to as "Efs"), *Enterococcus faecium* (hereinafter, referred to as "Efm"), *Enterococcus gallinarum* (hereinafter, referred to as "Eg"), and *Enterococcus casseliflavus* (hereinafter, referred to as "Ec") were selected. The selection was made through a comparative analysis of genomic sequences of an *Enterococcus* sp. microorganism to select regions specific for the four species as target sequences. Specifically, in the case of *Enterococcus gallinarum* ddl2 gene, gi62632242, gi62632240, and gi1244571, in the case of *Enterococcus faecalis* ldh, gi29374661, and gi307638684, in the case of *Enterococcus faecium* ldh, gi484100370, gi389867183, and gi388532432, in the case of *Enterococcus casseliflavus* ldh, gi482850047, and gi325573643 were aligned by using a Clustalx2 program and specific regions for the species were obtained to design a primer and a probe.

As a result, a primer set for target sequences of four *Enterococcus* species, in other words, *Enterococcus faecalis* ldh gene, *Enterococcus faecium* ldh gene, *Enterococcus gallinarum* ddl2 gene, and *Enterococcus casseliflavus* ldh gene were selected. Detailed properties of the primer set are as described in Table 1.

TABLE 1

| Primer | | SEQ. ID. NO: | Size | Tm (° C.) | Estimated PCR product length (bp) |
|---|---|---|---|---|---|
| *Enterococcus faecalis* ldh | Forward | 1 | 20 | 54.3 | 88 |
| | Reverse | 2 | 19 | 53.0 | |
| *Enterococcus faecium* ldh | Forward | 4 | 19 | 50.9 | 80 |
| | Reverse | 5 | 21 | 53.4 | |
| *Enterococcus gallinarum* ddl2 | Forward | 7 | 23 | 55.5 | 66 |
| | Reverse | 8 | 18 | 51.4 | |
| *Enterococcus casseliflavus* ldh | Forward | 10 | 18 | 53.8 | 96 |
| | Reverse | 11 | 20 | 54.3 | |

Thereafter, one of *Enterococcus faecalis* (CCARM5022), *Enterococcus faecium* (CCARM5024), *Enterococcus gallinarum* (CCARM5023), and *Enterococcus casseliflavus* (CCARM5027) obtained from Culture Collection of Antibiotic Resistant Strain Microbes were added to a reaction well in a certain number for each PCR ($10^3$, $10^2$, $10^1$, and $10^0$) and then each primer set shown in Table 1 was added thereto to perform PCR under the same conditions. The PCR was performed for 8 wells among 96 wells by using each of 8 primers under the same conditions as described above. The PCR was performed by using an LC480 apparatus (LightCycler, Roche) and thermocycling conditions included 45 cycles at a temperature of 95° C. for 2 seconds and at 60 for 10 seconds. A 2×PCR solution had the same composition as described below:

| | |
|---|---|
| 10x z-taq buffer (R006A, TaKaRa ™) | 20 ul |
| 25 mM dNTP | 16 ul |
| z-Taq (R006A, TaKaRa ™) | 2 ul |
| forward primer/reverse primer/probe mix (final 1 uM:1 uM:400 nM) | 10 ul |
| water | 52 ul |
| total volume of reaction solution | 100 ul |

Reaction solutions including each of the four primer sets were used to perform a single PCR and amplification products obtained therefrom were analyzed by using a Bioanalyzer 2100 (Agilent), which suggested that single amplification products were produced. Also, results shown in Table 2 were obtained. The amplification results were analyzed by measuring Tm of the amplification products in real-time to confirm whether the amplification products were produced or produced without a byproduct. It was concluded that the results obtained therefrom coincided with the results analyzed by using the Bioanalyzer 2100 (Agilent).

TABLE 2

| Sample (Cells/reaction) | Ec | Efm | Efs | Eg |
|---|---|---|---|---|
| $10^3$ | 83.07 | 77.44 | 77.59 | 76.44 |
| $10^2$ | 83.11 | 77.42 | 77.59 | 76.38 |
| 10 | 82.88 | 77.54 | 77.58 | 76.37 |
| 1 | — | 73.61 | 77.54 | 76.32 |

In Table 2, Ec, Efm, Efs and Eg, which respectively represent *Enterococcus casseliflavus*, *Enterococcus faecium*, *Enterococcus faecalis*, and *Enterococcus gallinarum*, and Tm values of the amplification products are shown in the unit of ° C.

As shown in Table 2, one bacterium was detected for each reaction solution, except for *Enterococcus casseliflavus*. Also, a Tm value obtained therefrom was obtained as a single value and thus, detection specificity was high.

FIG. 1 shows amplification results of real-time PCR by using each of primer sets in Table 1. The real-time PCR was performed as a single PCR including each of a first probe including a nucleotide sequence of SEQ ID NO: 3; a second probe including a nucleotide sequence of SEQ ID NO: 6; a third probe including a nucleotide sequence of SEQ ID NO: 9; and a fourth probe including a nucleotide sequence of SEQ ID NO: 12. The real-time detection was performed by using a Taqman® PCR assay. In FIG. 1, "Efm", "Efs", "Eg", and "Ec" represents *Enterococcus faecium*, *Enterococcus faecalis*, *Enterococcus gallinarum*, and *Enterococcus casseliflavus*, respectively, and "$10^3$", "$10^2$", "$10^1$", and "$10^0$" represents the concentration of the indicated bacterial cells per liter.

Figure 2:
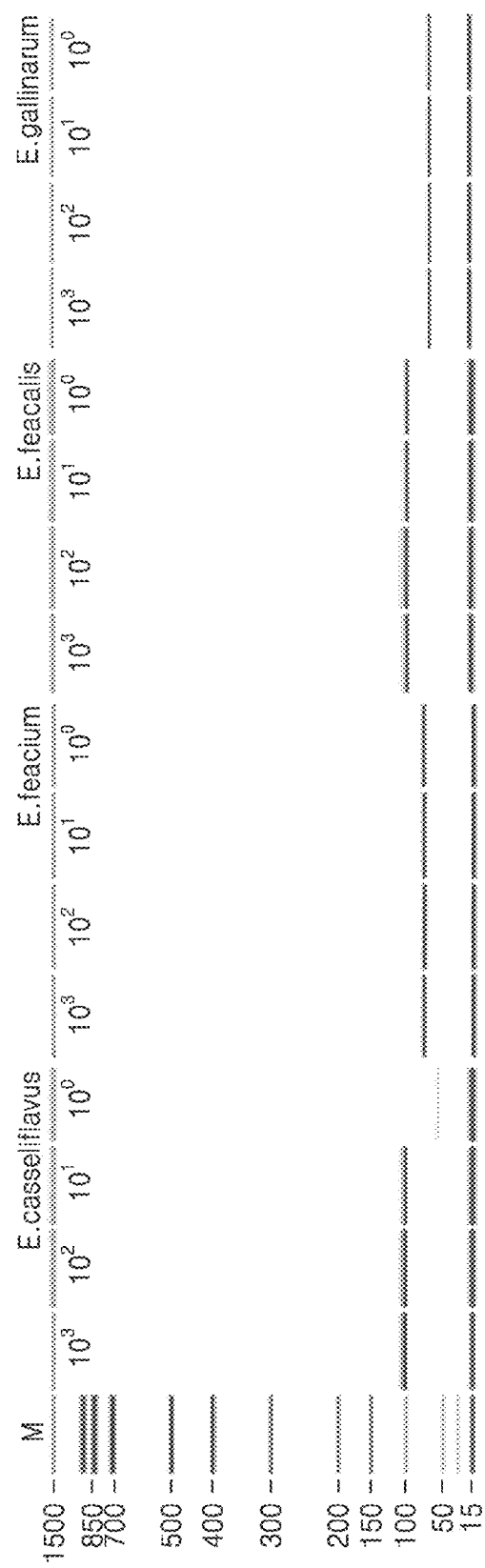
FIG. 2 shows an electrophoretic separation of the amplification products of real-time PCR using primer sets in Table 1.

FIG. 2 shows electrophoresis results of the amplification products. In FIG. 2, the first lane M is a size marker, which includes single bands for target amplification products that were specifically designed according to different *Enterococcus* species. This suggests that even the genes of several copies may be detected.

(2) Design of a Primer Set for Detection of Four Vancomycin Resistance Genes and Confirmation of Properties Thereof First, a primer set suitable for specifically detecting four vancomycin resistance genes, in other words, VanA gene, VanB gene, VanC1 gene, and VanC2/C3 gene, was selected. The selection was made through a comparative analysis of genomic sequences of the genes of an *Enterococcus* sp. microorganism to select regions specific for the four genes as target sequences. In more detail, 5 to 10 of each genomic sequence obtained from NCBI were aligned by using Clustalx2 to identify specific regions, and suitable factors for high speed PCR were combined thereto, which were designed to produce short amplification products.

As a result, a primer set that specifically binds to four vancomycin resistance genes was selected. Detailed properties of the primer set are as shown in Table 3.

TABLE 3

| Primer | | SEQ. ID. NO: | Size | Tm (° C.) | Estimated PCR product length (bp) |
|---|---|---|---|---|---|
| VanA | Forward | 13 | 22 | 62.1 | 68 |
| | Reverse | 14 | 23 | 62.9 | |
| VanB | Forward | 16 | 18 | 56.3 | 77 |
| | Reverse | 17 | 22 | 58.4 | |
| VanC1 | Forward | 19 | 25 | 64.1 | 63 |
| | Reverse | 20 | 22 | 60.1 | |
| VanC2/C3 | Forward | 22 | 18 | 53.8 | 79 |
| | Reverse | 23 | 18 | 53.8 | |

Thereafter, vancomycin-resistant Enterococci (CCARM5022, CCARM5024, CCARM5023, CCARM5027) obtained from Culture Collection of Antibiotic Resistant Strain Microbes were added to a reaction well in a certain amount of cells ($10^3$, $10^2$, 10, and 1) per each PCR reaction and then a two set combination, a three set combination, and a four set combination selected from the primer sets in Table 3 were added to the well to perform a multiplex real time-PCR. The PCR was performed by using an LC480 apparatus (LightCycler, Roche) and thermocycle conditions included 45 cycles at a temperature of 95° C. for 2 seconds and at 60° C. for 10 seconds. In the case of a double PCR, a 2×PCR solution had the following composition:

| | |
|---|---|
| 10x z-taq buffer (R006A, TaKaRa ™) | 20 ul |
| 25 mM dNTP | 16 ul |
| z-Taq enzymatic (R006A, TaKaRa ™) | 4 ul |
| first forward primer/reverse primer/probe mix (final 1 uM:1 uM:400 nM) | 10 ul |
| second forward primer/reverse primer/probe mix (final 1 uM:1 uM:400 nM) | 12 ul |
| water | 38 ul |
| total volume of reaction solution | 100 ul |

The probes used were a fifth probe including a nucleotide sequence of SEQ ID NO: 15; a sixth probe including a nucleotide sequence of SEQ ID NO: 18; a seventh probe including a nucleotide sequence of SEQ ID NO: 21: and an eighth probe including a nucleotide sequence of SEQ ID NO: 24. 5' and 3' ends of the probe were labeled with FAM and -NFQ-MGB, respectively.

Figure 3:
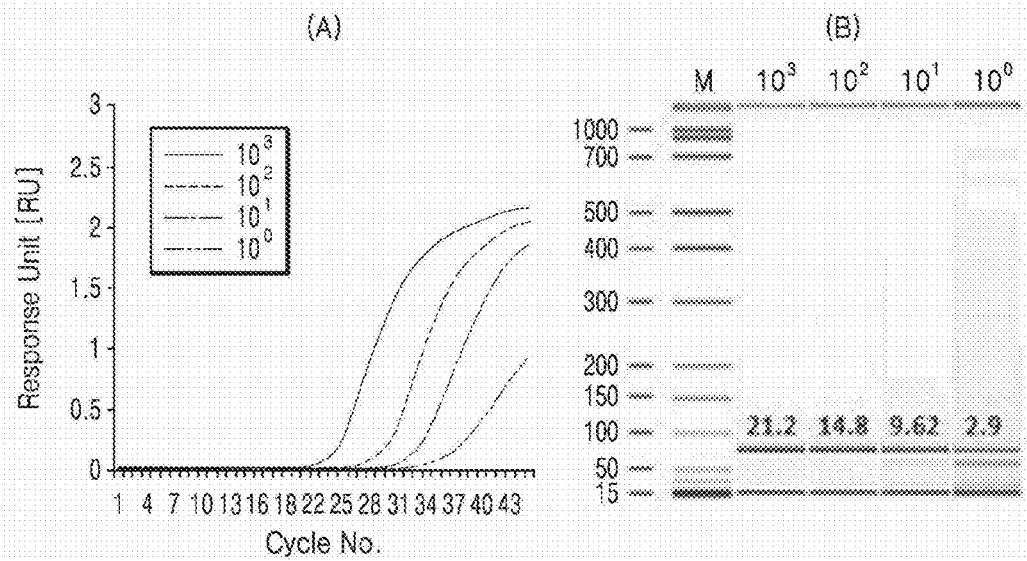
FIG. 3 shows real-time PCR results with respect to wells that include a VanA specific primer set and a VanB specific primer set, including (A) a PCR curve that shows the amount of VanA according to time and (B) an electrophoresis image thereof.

FIG. 3 shows real-time PCR results with respect to wells that include a VanA specific primer set and a VanB specific primer set, including (A) a PCR curve that shows the amount of VanA according to time and (B) an electrophoresis image thereof.

Figure 4:
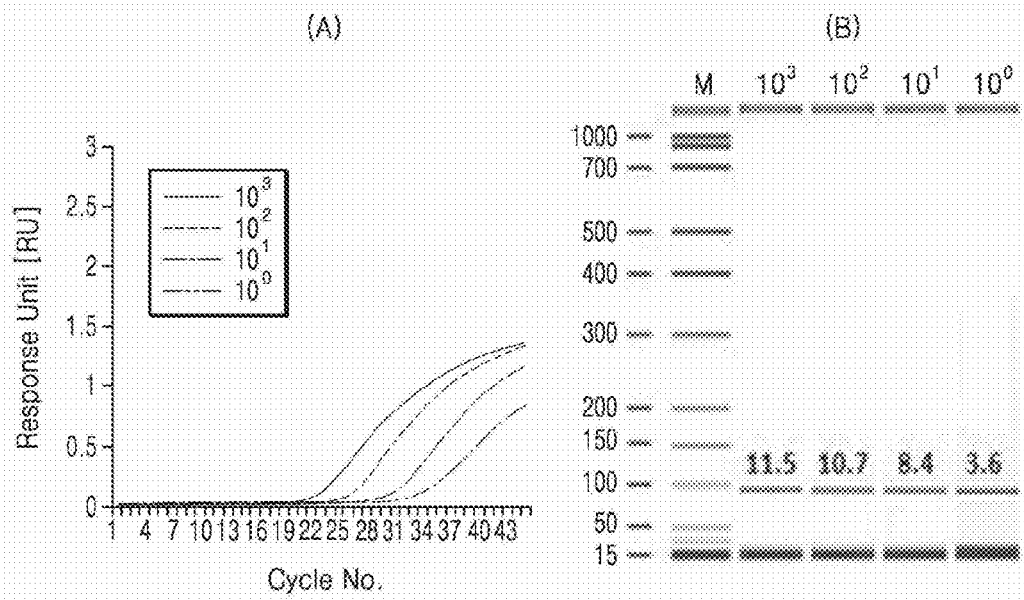
FIG. 4 shows real-time PCR results with respect to wells that include a VanA specific primer set and a VanB specific primer set, including (A) a PCR curve that shows the amount of VanB according to time and (B) an electrophoresis image thereof.

FIG. 4 shows real-time PCR results with respect to wells that include a VanA specific primer set and a VanB specific primer set, including (A) a PCR curve that shows the amount of VanB according to time and (B) an electrophoresis image thereof.

Figure 5:
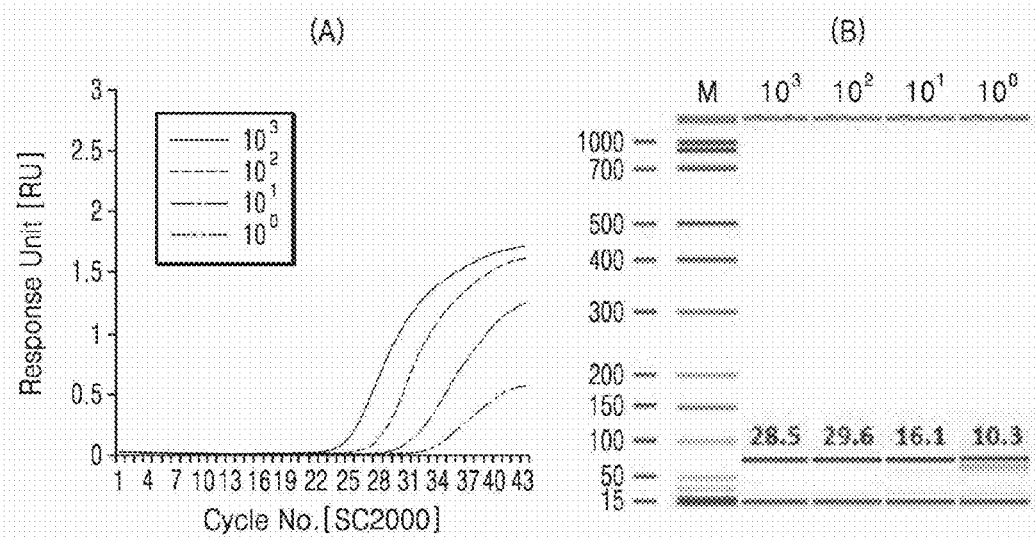
FIG. 5 shows real-time PCR results with respect to wells that include a VanC specific primer set and a VanC2/C3 specific primer set, including (A) a PCR curve that shows the amount of VanC according to time and (B) an electrophoresis image thereof.

FIG. 5 shows real-time PCR results with respect to wells that include a VanC specific primer set and a VanC2/C3 specific primer set, including (A) a PCR curve that shows the amount of VanC according to time and (B) an electrophoresis image thereof.

Figure 6:
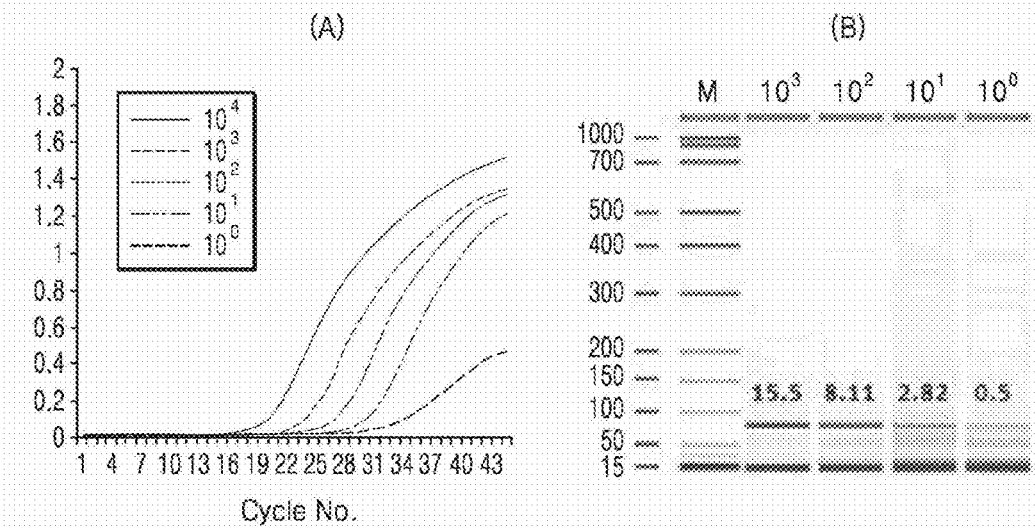
FIG. 6 shows real-time PCR results with respect to wells that include a VanC specific primer set and a VanC2/C3 specific primer set, including (A) a PCR curve that shows the amount of VanC2/C3 according to time and (B) an electrophoresis image thereof.

FIG. 6 shows real-time PCR results with respect to wells that include a VanC specific primer set and a VanC2/C3 specific primer set, including (A) a PCR curve that shows the amount of Van C2/C3 according to time and (B) an electrophoresis image thereof.

In FIGS. 3 to 6, the vertical axis is a response unit measuring fluorescence emitted from FAM, the horizontal axis is a cycle number, M is a size marker, and each of $10^3$, $10^2$, $10^1$, and $10^0$ represents the specific number of *Enterococcus* for each reaction solution. In FIGS. 3 and 4, the presence of VanA and VanB genes was confirmed by using vancomycin-resistant *Enterococcus* CCARM 5024 (*E. feacium*) and CCARM 5022 (*E. feacalis*), respectively. In FIGS. 5 and 6, the presence of VanC1 and VanC2/3 was confirmed by using vancomycin-resistant *Enterococcus* CCARM 5023 (*E. gallinarum*) and CCARM 5027 (*E. casselilfavus*) strains. As shown in FIGS. 3 to 6, from 2 to 8 cells were detected for each reaction solution.

Thereafter, with respect to *Enterococcus* genus species having one of four vancomycin resistance genes, primer sets specific for VanA, VanB, VanC1, and VanC2/3 were used for PCR amplification to detect target nucleic acid amplification, specificity of detection, and analytical specificity according to the method described above. PCR conditions were as described above. As shown in Table 4, a multiplex PCR including primers specific for each vancomycin resistance gene was used to detect up to 1 *Enterococcus* for each reaction solution.

TABLE 4

| Van gene type | Strain number | VanA (copy/ reaction solution) | VanB (copy/ reaction solution) | VanC1 (copy/ reaction solution) | VanC2/3 (copy/ reaction solution) |
|---|---|---|---|---|---|
| vanA | CCARM 5024 | 10⁰ or greater | ND | ND | ND |
| vanB | CCARM 5022 | ND | 10⁰ or greater | ND | ND |
| vanC1 | CCARM 5020 | ND | ND | 10⁰ or greater | ND |
| vanC2/3 | CCARM 5027 | ND | ND | ND | 10⁰ or greater |

Also, PCR was performed to by using the primer set specific for four vancomycin resistance genes, namely, VanA gene, VanB gene, VanC1 gene, and VanC2/3 gene as primers and genomes of 33 species of vancomycin-resistant *Enterococcus* as templates measure inclusivity and specificity. PCR conditions were as described below. gDNA of each strain was gDNA that passed through QC in ATCC, NCTC, and CCARM, which was subjected to PCR according to an FDA guide by using $10^5$-$10^6$ of gDNA as a template. As a result, 33 species shown in Table 5 were detected.

TABLE 5

| | | | Reference | Genotyping results according to the Example | | | | |
|---|---|---|---|---|---|---|---|---|
| No. | Individual | VRE-strain No. | Genotype | VanA | VanB | VanC1 | VanC2/C3 | Genotype |
| 1 | Efm, NJ-3 | ATCC 51299 | VanB1 | x | ○ | x | x | VanB |
| 2 | Efm, VRE | ATCC 70022 | VanA | ○ | x | x | x | VanA |
| 3 | Efs, Taxo 239 | ATCC 51575 | unknown | x | ○ | x | x | VanB |
| 4 | Eg | ATCC 49573 | VanC1 | x | x | ○ | x | VanC1 |
| 5 | ec | ATCC 25788 | VanC2/C3 | x | x | x | ○ | VanC2/C3 |
| 6 | Efs | ATCC 29212 | unknown | x | x | x | x | VSE |
| 7 | Efm | ATCC 19434 | VanD | x | x | x | x | VSE |
| 8 | Eg | ATCC BAA-748 | unknown | x | x | ○ | x | VanC1 |
| 9 | Ec | ATCC 700327 | unknown | x | x | x | ○ | VanC2/C3 |
| 10 | Efm, MMC4 | ATCC 51559 | VanA | ○ | x | x | x | VanA |
| 11 | Efs, V583 | ATCC 700802 | VanB | x | ○ | x | x | VanB |
| 12 | Efs | CCARM 0011 | unknown | x | x | x | x | VSE |
| 13 | Efm | CCARM 5108 | VSE | x | x | x | x | VSE |
| 14 | Efs | CCARM 5177 | VSE | x | x | x | x | VSE |
| 15 | Efm | CCARM 5262 | VSE | x | x | x | x | VSE |
| 16 | Efm | CCARM 5223 | VSE | x | x | x | x | VSE |
| 17 | Efs | CCARM 5115 | VSE | x | x | x | x | VSE |
| 18 | Efs | CCARM 5200 | VSE | x | x | x | x | VSE |
| 19 | Efs | CCARM 5196 | VSE | x | x | x | x | VSE |
| 20 | Efs | ATCC 29200 | VanE | x | x | x | x | VSE |
| 21 | Efs | CCARM 5021 | VanA | ○ | x | x | x | VanA |
| 22 | Efm | CCARM 5004 | VanA | ○ | x | x | x | VanA |
| 23 | Efm | CCARM 5011 | VanA | ○ | x | x | x | VanA |
| 24 | Efs | CCARM 5025 | VanB | x | ○ | x | x | VanB |
| 25 | Efs | CCARM 5013 | VanB | x | ○ | x | x | VanB |
| 26 | Efs | CCARM 5022 | VanB | x | ○ | x | x | VanB |
| 27 | Efs | CCARM 5015 | VanB | x | ○ | x | x | VanB |
| 28 | Eg | CCARM 5023 | VanC | x | x | ○ | x | VanC1 |
| 29 | Eg | CCARM 5026 | VanC1 | x | x | ○ | x | VanC1 |
| 30 | Eg | CCARM 5020 | VanC1 | x | x | ○ | x | VanC1 |
| 31 | Ec | CCARM 5017 | VanC2 | x | x | x | ○ | VanC2/C3 |
| 32 | Ec | CCARM 5027 | VanC2 | x | x | x | ○ | VanC2/C3 |
| 33 | Efm | CCARM 5024 | VanA | ○ | x | x | x | VanA |

In Table 5, Ec, Efm, Efs, and Eg represent *Enterococcus casseliflavus*, *Enterococcus faecium*, *Enterococcus faecalis*, and *Enterococcus gallinarum*, respectively. VSE represents Vancomycin-susceptible *Enterococcus*.

Also, a primer set specific for four vancomycin resistance genes, which were VanA gene, VanB gene, VanC1 gene, and VanC2/3 gene as primers and 105 species of vancomycin-resistant microorganisms were used as a template for PCR amplification to measure exclusivity and specificity. PCR conditions were the same as described above. 105 types of species used in the PCR were used by obtaining gDNA from a culture collection, and according to the FDA guide, $10^6$-$10^7$ of gDNA were used as a template to perform PCR, to thereby confirm the occurrence of a cross reaction. As a result, as shown in Tables 6 to 8, 105 species that were not *Enterococcus* genus strains did not show the cross reaction.

TABLE 6

| No. | Bank No. | Organism (VRE) | vanA | vanB | vanC1 | vanC2/3 |
|---|---|---|---|---|---|---|
| 1 | ATCC 19606 | *Acinetobacter baumannii* | ND | ND | ND | ND |
| 2 | ATCC 7966 | *Aeromonas hydrophila* | ND | ND | ND | ND |
| 3 | ATCC 8750 | *Alcaligenes faecalis* subsp. *faecalis* | ND | ND | ND | ND |
| 4 | ATCC 10702 | *Bacillus cereus* | ND | ND | ND | ND |
| 5 | ATCC 15703 | *Bifidobacterium adolescentis* | ND | ND | ND | ND |
| 6 | ATCC 15697 | *Bifidobacterium longum* | ND | ND | ND | ND |
| 7 | BAA-1061 | *Campylobacter coli* | ND | ND | ND | ND |
| 8 | ATCC 33292 | *Campylobacter jejuni* sub sp. *jejuni* | ND | ND | ND | ND |
| 9 | ATCC 10231 | *Candida albicans* | ND | ND | ND | ND |
| 10 | VR-879 | *Chlamydia trachomatis* | ND | ND | ND | ND |
| 11 | ATCC 8090 | *Citrobacter freundii* | ND | ND | ND | ND |
| 12 | BAA-895 | *Citrobacter koseri* | ND | ND | ND | ND |
| 13 | ATCC 13124 | *Clostridium perfringens* | ND | ND | ND | ND |
| 14 | ATCC 11437 | *Clostridium sporogenes* | ND | ND | ND | ND |
| 15 | ATCC 25559 | *Eggerthella lenta* | ND | ND | ND | ND |
| 16 | ATCC 15038 | *Enterobacter aerogenes* | ND | ND | ND | ND |
| 17 | ATCC 13047 | *Enterobacter cloacae* | ND | ND | ND | ND |
| 18 | ATCC 10541 | *Enterococcus hirae* | ND | ND | ND | ND |
| 19 | ATCC 35401 | *Escherichia coli* | ND | ND | ND | ND |
| 20 | ATCC 35469 | *Escherichia fergusonii* | ND | ND | ND | ND |
| 21 | ATCC 49145 | *Gardnerella vaginalis* | ND | ND | ND | ND |
| 22 | ATCC 43504 | *Helicobacter pylori* | ND | ND | ND | ND |
| 23 | CRL-2221 | *Homo sapiens* | ND | ND | ND | ND |
| 24 | ATCC 700324 | *Klebsiella oxytoca* | ND | ND | ND | ND |
| 25 | ATCC 700603 | *Klebsiella pneumoniae* subsp. Pneumoniae | ND | ND | ND | ND |
| 26 | ATCC 4357 | *Lactobacillus acidophilus* | ND | ND | ND | ND |
| 27 | ATCC 23272 | *Lactobacillus reuteri* | ND | ND | ND | ND |
| 28 | ATCC 19435 | *Lactococcus lactis* | ND | ND | ND | ND |
| 29 | BAA-680 | *Listeria innocua* | ND | ND | ND | ND |
| 30 | ATCC 19114 | *Listeria monocytogenes* | ND | ND | ND | ND |
| 31 | ATCC 49031 | *Peptostreptococcus anaerobius* | ND | ND | ND | ND |
| 32 | ATCC 51903 | *Plesiomonas shigelloides* | ND | ND | ND | ND |
| 33 | ATCC 25845 | *Prevotella melaninogenica* | ND | ND | ND | ND |
| 34 | ATCC 12453 | *Proteus mirabilis* | ND | ND | ND | ND |
| 35 | ATCC 33672 | *Providencia stuartli* | ND | ND | ND | ND |
| 36 | ATCC 15442 | *Pseudomonas aeruginosa* | ND | ND | ND | ND |
| 37 | ATCC 700007 | *Pseudomonas putida* | ND | ND | ND | ND |
| 38 | BAA-731 | *Salmonella choleraesuis* (typhimurium) | ND | ND | ND | ND |
| 39 | BAA-1577 | *Salmonella enterica* subsp. *arizonae* | ND | ND | ND | ND |
| 40 | BAA-1584 | *Salmonella enterica* subsp. *Enterica* | ND | ND | ND | ND |
| 41 | ATCC 27137 | *Serratia marcescens* | ND | ND | ND | ND |
| 42 | BAA 1717 | *Staphylococcus aureus* | ND | ND | ND | ND |
| 43 | ATCC 12228 | *Staphylococcus epidermidis* | ND | ND | ND | ND |
| 44 | ATCC 13637 | *Stenotrophomonas maltophilia* | ND | ND | ND | ND |
| 45 | BAA-1138 | *Streptococcus agalactiae* | ND | ND | ND | ND |
| 46 | BAA-854 | *Streptococcus uberis* | ND | ND | ND | ND |
| 47 | ATCC 10790 | *Veillonella parvula* | ND | ND | ND | ND |
| 48 | ATCC 17802 | *Vibrio parahaemolyticus* | ND | ND | ND | ND |
| 49 | NCTC 0302163v | Cytomegalovirus | ND | ND | ND | ND |
| 50 | NCTC 0812214v | Enterovirus | ND | ND | ND | ND |

TABLE 7

| No. | Bank No. | Organism (VRE) | vanA | vanB | vanC1 | vanC2/3 |
|---|---|---|---|---|---|---|
| 51 | NCTC 0812218v | Enterovirus | ND | ND | ND | ND |
| 52 | ATCC 15309 | *Acinetobacter lwoffii* | ND | ND | ND | ND |
| 53 | ATCC 35098 | *Anaerococcus tetradius* | ND | ND | ND | ND |
| 54 | ATCC 43185 | *Bacteroides caccae* | ND | ND | ND | ND |
| 55 | ATCC 43183 | *Bacteroides stercoris* | ND | ND | ND | ND |
| 56 | ATCC 10565 | *Candida catenulata* | ND | ND | ND | ND |
| 57 | ATCC 33431 | *Cedecea davisae* | ND | ND | ND | ND |
| 58 | ATCC 25405 | *Citrobacter amalonaticus* | ND | ND | ND | ND |
| 59 | ATCC 51115 | *Citrobacter sedlakii* | ND | ND | ND | ND |
| 60 | ATCC 8260 | *Clostridium beijerinckii* | ND | ND | ND | ND |
| 61 | ATCC 638 | *Clostridium bifermentans* | ND | ND | ND | ND |
| 62 | ATCC 859 | *Clostridium butyricum* | ND | ND | ND | ND |
| 63 | ATCC 11957 | *Clostridium chauvoei* | ND | ND | ND | ND |
| 64 | ATCC 19400 | *Clostridium fallax* | ND | ND | ND | ND |
| 65 | ATCC 19401 | *Clostridium histolyticum* | ND | ND | ND | ND |
| 66 | ATCC 14501 | *Clostridium innocuum* | ND | ND | ND | ND |

TABLE 7-continued

| No. | Bank No. | Organism | VanA | VanB | VanC1 | VanC2/3 |
|---|---|---|---|---|---|---|
| 67 | ATCC 19402 | *Clostridium novyi* | ND | ND | ND | ND |
| 68 | ATCC 49531 | *Clostridium orbiscindens* | ND | ND | ND | ND |
| 69 | ATCC 25780 | *Clostridium paraputrificum* | ND | ND | ND | ND |
| 70 | ATCC 25582 | *Clostridium ramosum* | ND | ND | ND | ND |
| 71 | ATCC 35704 | *Clostridium scindens* | ND | ND | ND | ND |
| 72 | ATCC 9714 | *Clostridium sordellii* | ND | ND | ND | ND |
| 73 | ATCC 19403 | *Clostridium sphenoides* | ND | ND | ND | ND |
| 74 | ATCC 29900 | *Clostridium spiroforme* | ND | ND | ND | ND |
| 75 | ATCC 14940 | *Clostridium symbiosum* | ND | ND | ND | ND |
| 76 | ATCC 19405 | *Clostridium tertium* | ND | ND | ND | ND |
| 77 | ATCC 19406 | *Clostridium tetani* | ND | ND | ND | ND |
| 78 | ATCC 33030 | *Corynebacterium genitalium* | ND | ND | ND | ND |
| 79 | ATCC 15947 | *Edwardsiella tarda* | ND | ND | ND | ND |
| 80 | ATCC 43198 | *Enterococcus cecorum* | ND | ND | ND | ND |
| 81 | ATCC 51266 | *Enterococcus dispar* | ND | ND | ND | ND |
| 82 | ATCC 49427 | *Enterococcus raffinosus* | ND | ND | ND | ND |
| 83 | ATCC 33650 | *Escherichia hermannii* | ND | ND | ND | ND |
| 84 | ATCC 8501 | *Fusobacterium varium* | ND | ND | ND | ND |
| 85 | ATCC 27824 | *Gemella morbillorum* | ND | ND | ND | ND |
| 86 | ATCC 13337 | *Hafnia alvei* | ND | ND | ND | ND |
| 87 | ATCC 33999 | *Leminorella grimontii* | ND | ND | ND | ND |
| 88 | ATCC 19120 | *Listeria grayi* | ND | ND | ND | ND |
| 89 | ATCC 14963 | *Peptoniphilus asaccharolyticus* | ND | ND | ND | ND |
| 90 | ATCC 25260 | *Porphyromonas asaccharolytica* | ND | ND | ND | ND |
| 91 | ATCC 35198 | *Proteus penneri* | ND | ND | ND | ND |
| 92 | ATCC 9886 | *Providencia alcalifaciens* | ND | ND | ND | ND |
| 93 | ATCC 9250 | *Providencia rettgeri* | ND | ND | ND | ND |
| 94 | ATCC 27592 | *Serratia liquefaciens* | ND | ND | ND | ND |
| 95 | ATCC 9207 | *Shigella boydii* | ND | ND | ND | ND |
| 96 | ATCC 29930 | *Shigella sonnei* | ND | ND | ND | ND |
| 97 | ATCC 43078 | *Streptococcus dysgalactiae* | ND | ND | ND | ND |
| 98 | ATCC 27335 | *Streptococcus intermedius* | ND | ND | ND | ND |
| 99 | ATCC 43970 | *Yersinia bercovieri* | ND | ND | ND | ND |

| No. | Bank No. | Organism (VRE) | VanA | VanB | VanC1 | VanC2/3 |
|---|---|---|---|---|---|---|
| 100 | ATCC 49176 | *Abiotrophia defectiva* | ND | ND | ND | ND |
| 101 | ATCC 27757 | *Clostridium nexile* | ND | ND | ND | ND |

In table 6 and 7, the term "VRE" represents "vancomycin resistant *Enterococcus*".

TABLE 8

| 102 | ATCC 25986 | *Collinsella aerofaciens* | ND | ND | ND | ND |
|---|---|---|---|---|---|---|
| 103 | ATCC 43380 | *Yersinia rohdei* | ND | ND | ND | ND |
| 104 | ATCC 49490 | *Trabulsiella guamensis* | ND | ND | ND | ND |
| 105 | ATCC BAA-1803 | *Clostridium difficile* | ND | ND | ND | ND |

Example 2

Verification of VRE Infected Patient Samples

The first to fourth primer sets specific for *Enterococcus* specific genes, the fifth to eighth primer sets specific for four vancomycin resistance genes, and the first to eighth probes specific for the *Enterococcus* specific genes and the vancomycin resistance genes described in Example 1 were used to verify a VRE infection status of patient samples.

The PCR for verification was performed by using two primer sets from the first to the fourth primer sets and the fifth to the eighth primer sets, in other words, a VanA specific primer set and a VanB specific primer set; and a VanC1 specific primer set and a VanC2/C3 specific primer set, the first to the eighth probes, and 1 ul of patient sample was used as a template to perform PCR with a total amount of reaction solution of 20 ul.

In more detail, the PCR was performed by adding 1 ul of each of 10× serial dilution solution of a patient sample to a reaction well, and then adding each of the first to the fourth primer sets, or a VanA specific primer set and a VanB specific primer set; or a VanC1 specific primer set and a VanC2/C3 specific primer set, and the first to the eighth probes to each of 8 wells under the same condition. The PCR included the use of an LC480 apparatus (LightCycler, Roche) and 45 cycles of a thermocycle at a temperature of 95° C. for 2 seconds and at 60° C. for 10 seconds.

2×PCR solution (master mix) has the following composition:

| | |
|---|---|
| 10x z-taq buffer (R006A, TaKaRa) | 20 ul |
| 25 mM dNTP | 16 ul |
| z-Taq enzymatic (R006A, TaKaRa) | 4 ul |
| first forward primer/reverse primer/probe mix (final 1 uM:1 uM:400 nM) | 10 ul |
| second forward primer/reverse primer/probe mix (final 1 uM:1 uM:400 nM) | 12 ul |
| water | 38 ul |
| total volume of reaction solution | 100 ul |

53 samples were taken from 53 individuals that were verified to be VRE infected. Among them, 29 samples out of 53 samples were rectal cotton swabs and 24 were liquid culture solution. The liquid culture medium was obtained by obtaining a rectal cotton swab obtained from a patient, adding the swab to a blood culture medium (BHI, BD Difco), and then incubating in a shaking incubator with stirring within 3 days at a temperature of 37° C. As a control group, a VITEK® 2 system and a PCR kit (Roche) were used for the same sample to amplify and detect the target nucleic acid.

As a result, with respect to 52 clinical patient samples, which were reference samples, results of a single PCR of wells including each of primer set of the first primer set, the second primer set, the third primer set and the fourth primer set, or the VanA specific primer set and the VanB specific primer set from the four primer sets specific for the four vancomycin resistance genes described above or the VanC1 specific primer set and the VanC2/C3 specific primer set and the first to the eighth probes showed a concordance ratio of 98.1%, sensitivity of 100% (95% confidence interval (87.1-100)), and specificity of 96.1% (95% confidence interval (81.1-99.3)). The eight single PCRs were performed simultaneously under the same conditions.

As described above, the *Enterococcus* genus and antibiotic resistance were detected simultaneously.

It should be understood that the exemplary embodiments described therein should be considered in a descriptive sense only and not for purposes of limitation. Descriptions of features or aspects within each embodiment should typically be considered as available for other similar features or aspects in other embodiments.

While one or more embodiments of the present disclosure have been described with reference to the figures, it will be understood by those of ordinary skill in the art that various changes in form and details may be made therein without departing from the spirit and scope of the present invention as defined by the following claims.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A method of detecting at least one *Enterococcus* genus microorganism expressing a vancomycin resistance gene, the method comprising:
   (i) providing (a) at least one *Enterococcus* sp. specific primer set selected from the group consisting of
      a first primer set comprising a polynucleotide which comprises 10 or more contiguous nucleotides selected from a nucleotide sequence of SEQ ID NO: 1 and a polynucleotide that comprises 10 or more contiguous nucleotides selected from a nucleotide sequence of SEQ ID NO: 2;
      a second primer set comprising a polynucleotide which comprises 10 or more contiguous nucleotides selected from a nucleotide sequence of SEQ ID NO: 4 and a polynucleotide that comprises 10 or more contiguous nucleotides selected from SEQ ID NO: 5;
      a third primer set comprising a polynucleotide which comprises 10 or more contiguous nucleotides selected from a nucleotide sequence of SEQ ID NO: 7 and a polynucleotide that comprises 10 or more contiguous nucleotides selected from SEQ ID NO: 8; and
      a fourth primer set comprising a polynucleotide which comprises 10 or more contiguous nucleotides selected from a nucleotide sequence of SEQ ID NO: 10 and a polynucleotide that comprises 10 or more contiguous nucleotides selected from SEQ ID NO: 11;
   and (b) at least one vancomycin resistance gene specific primer set selected from the group consisting of
      a fifth primer set comprising a polynucleotide which comprises 10 or more contiguous nucleotides selected from a nucleotide sequence of SEQ ID NO: 13 and a polynucleotide that comprises 10 or more contiguous nucleotides selected from a nucleotide sequence of SEQ ID NO: 14;
      a sixth primer set comprising a polynucleotide which comprises 10 or more contiguous nucleotides selected from a nucleotide sequence of SEQ ID NO: 16 and a polynucleotide that comprises 10 or more contiguous nucleotides selected from SEQ ID NO: 17;
      a seventh primer set comprising a polynucleotide which comprises 10 or more contiguous nucleotides selected from a nucleotide sequence of SEQ ID NO: 19 and a polynucleotide that comprises 10 or more contiguous nucleotides selected from SEQ ID NO: 20; and
      an eighth primer set comprising a polynucleotide which comprises 10 or more contiguous nucleotides selected from a nucleotide sequence of SEQ ID NO: 22 and a polynucleotide that comprises 10 or more contiguous nucleotides selected from SEQ ID NO: 23;
   (ii) contacting the primer set specific for at least one *Enterococcus* and the primer set specific for at least one vancomycin resistance gene with a sample that is suspected to comprise at least one *Enterococcus* genus microorganism expressing or comprising a vancomycin resistance gene,
   wherein the first primer set, the second primer set, the third primer set, the fourth primer set, the fifth primer set, the sixth primer set, the seventh primer set, and the eighth primer set are for the amplification of an *Enterococcus faecalis* lactate dehydrogenase gene (ldh), an *Enterococcus faecium* lactate dehydrogenase gene (ldh), *Enterococcus gallinarum* D-alanine: D-alanine ligase gene2 (ddl2), an *Enterococcus casseliflavus* lactate dehydrogenase gene (ldh), a VanA gene, a VanB gene, a VanC1 gene, and a VanC2/3 gene, respectively;
   (iii) elongating the primers hybridized with a target nucleic acid to amplify the target nucleic acid and provide an amplification product; and (iv) identifying the presence of the target nucleic acid in the sample on the basis of the amplification product.

2. The method of claim 1, wherein the primers of each primer set are labeled by a different label.

3. The method of claim 1, wherein
the presence of an amplification product of the first primer set indicates that *Enterococcus faecalis* exists in the sample,
the presence of an amplification product of the second primer set indicates that *Enterococcus faecium* exists in the sample,
the presence of an amplification product of the third primer set indicates that *Enterococcus gallinarum* exists in the sample,
the presence of an amplification product of the fourth primer set indicates that *Enterococcus casseliflavus* exists in the sample,
the presence of an amplification product of the fifth primer set indicates that a VanA resistant microorganism exists in the sample,
the presence of an amplification product of the sixth primer set indicates that a VanB resistant microorganism exists in the sample,
the presence of an amplification product of the seventh primer set indicates that a VanC1 resistant microorganism exists in the sample, and
the presence of an amplification product of the eighth primer set indicates that a VanC2/3 resistant microorganism exists in the sample.

4. The method of claim 1, wherein the sample is a biological sample.

5. The method of claim 1, wherein the sample is urine, mucus, saliva, tears, blood, plasma, serum, sputum, spinal fluid, pleural fluid, nipple aspirates, lymph, respiratory tract fluid, serous, urogenital canal fluid, breast milk, lymphatic fluid, semen, cerebrospinal fluid, body fluid of an organ system, ascites, cystic tumor fluid, amniotic fluid, rectal swab, or a combination thereof.

6. The method of claim 1, wherein identifying the presence of the target nucleic acid in the amplification product further comprises hybridizing the amplification product to a probe specific for the amplification product.

7. The method of claim 6, wherein the method comprises contacting the amplification product with at least one probe selected from the group consisting of
a first probe comprising 10 or more contiguous nucleotides selected from a nucleotide sequence of SEQ ID NO: 3;
a second probe comprising 10 or more contiguous nucleotides selected from a nucleotide sequence of SEQ ID NO: 6;
a third probe comprising 10 or more contiguous nucleotides selected from a nucleotide sequence of SEQ ID NO: 9;
a fourth probe comprising 10 or more contiguous nucleotides selected from a nucleotide sequence of SEQ ID NO: 12;
a fifth probe comprising 10 or more contiguous nucleotides selected from a nucleotide sequence of SEQ ID NO: 15;
a sixth probe comprising 10 or more contiguous nucleotides selected from a nucleotide sequence of SEQ ID NO: 18;
a seventh probe comprising 10 or more contiguous nucleotides selected from a nucleotide sequence of SEQ ID NO: 21; and
an eighth probe comprising 10 or more contiguous nucleotides selected from a nucleotide sequence of SEQ ID NO: 24.

8. The method of claim 7, wherein the probe comprises a detectable label.

9. The method of claim 1, further comprising separating nucleic acid from a sample and, optionally, incubating the sample to specifically proliferate the *Enterococcus* genus microorganism before the separating the nucleic acid.

10. A kit comprising:
(a) at least one *Enterococcus* species specific primer set selected from the group consisting of
a first primer set comprising a polynucleotide which comprises 10 or more contiguous nucleotides selected from a nucleotide sequence of SEQ ID NOs. 1 and a polynucleotide that comprises 10 or more contiguous nucleotides selected from a nucleotide sequence of SEQ ID NO: 2;
a second primer set comprising a polynucleotide which comprises 10 or more contiguous nucleotides selected from a nucleotide sequence of SEQ ID NO: 4 and a polynucleotide that comprises 10 or more contiguous nucleotides selected from SEQ ID NO: 5;
a third primer set comprising a polynucleotide which comprises 10 or more contiguous nucleotides selected from a nucleotide sequence of SEQ ID NO: 7 and a polynucleotide that comprises 10 or more contiguous nucleotides selected from SEQ ID NO: 8; and
a fourth primer set comprising a polynucleotide which comprises 10 or more contiguous nucleotides selected from a nucleotide sequence of SEQ ID NO: 10 and a polynucleotide that comprises 10 or more contiguous nucleotides selected from SEQ ID NO: 11;
(b) and at least one vancomycin resistance gene specific primer set selected from the group consisting of
a fifth primer set comprising a polynucleotide which comprises 10 or more contiguous nucleotides selected from a nucleotide sequence of SEQ ID NO: 13 and a polynucleotide that comprises 10 or more contiguous nucleotides selected from a nucleotide sequence of SEQ ID NO: 14;
a sixth primer set comprising a polynucleotide which comprises 10 or more contiguous nucleotides selected from a nucleotide sequence of SEQ ID NO: 16 and a polynucleotide that comprises 10 or more contiguous nucleotides selected from SEQ ID NO: 17;
a seventh primer set comprising a polynucleotide which comprises 10 or more contiguous nucleotides selected from a nucleotide sequence of SEQ ID NO: 19 and a polynucleotide that comprises 10 or more contiguous nucleotides selected from SEQ ID NO: 20; and
an eighth primer set comprising a polynucleotide which comprises 10 or more contiguous nucleotides selected from a nucleotide sequence of SEQ ID NO: 22 and a polynucleotide that comprises 10 or more contiguous nucleotides selected from SEQ ID NO: 23;
wherein the first primer set, second primer set, third primer set, fourth primer set, fifth primer set, sixth primer set, seventh primer set, and eighth primer set hybridize to *Enterococcus faecalis* lactate dehydrogenase gene (ldh), an *Enterococcus faecium* lactate dehydrogenase gene (ldh), an *Enterococcus gallinarum*

D-alanine:D-alanine ligase gene2 (ddl2), an *Enterococcus casseliflavus* lactate dehydrogenase gene (ldh), a VanA gene, a VanB gene, a VanC1 gene, and a VanC2/3 gene, respectively;

and wherein (i) the least one *Enterococcus* species specific primer set, the at least one vancomycin resistance gene specific primer set, or both comprise a detectable label; or (ii) the kit further comprises a probe comprising a detectable label for the amplification products of the least one *Enterococcus* species specific primer set and/or a probe comprising a detectable label for the amplification product of the at least one vancomycin resistance gene specific primer set; or both (i) and (ii).

11. The kit of claim 10, further comprising at least one of
a first probe comprising 10 or more contiguous nucleotides selected from a nucleotide sequence of SEQ ID NO: 3;
a second probe comprising 10 or more contiguous nucleotides selected from a nucleotide sequence of SEQ ID NO: 6;
a third probe comprising 10 or more contiguous nucleotides selected from a nucleotide sequence of SEQ ID NO: 9;
a fourth probe comprising 10 or more contiguous nucleotides selected from a nucleotide sequence of SEQ ID NO: 12;
a fifth probe comprising 10 or more contiguous nucleotides selected from a nucleotide sequence of SEQ ID NO: 15;
a sixth probe comprising 10 or more contiguous nucleotides selected from a nucleotide sequence of SEQ ID NO: 18;
a seventh probe comprising 10 or more contiguous nucleotides selected from a nucleotide sequence of SEQ ID NO: 21; and
an eighth probe comprising 10 or more contiguous nucleotides selected from a nucleotide sequence of SEQ ID NO: 24.

12. The kit of claim 11, wherein the first probe, the second probe, the third probe, the fourth probe, the fifth probe, the sixth probe, the seventh probe, and the eighth probe hybridize to an *Enterococcus faecalis* lactate dehydrogenase gene (ldh), an *Enterococcus faecium* lactate dehydrogenase gene (ldh), an *Enterococcus gallinarum* D-alanine:D-alanine ligase gene (ddl2), an *Enterococcus casseliflavus* lactate dehydrogenase gene (ldh), a VanA gene, a VanB gene, a VanC1 gene, and a VanC2/3 gene, respectively.

13. A composition comprising
(a) at least one *Enterococcus* species specific primer set selected from the group consisting of
a first primer set comprising a polynucleotide which comprises 10 or more contiguous nucleotides selected from a nucleotide sequence of SEQ ID NOs. 1 and a polynucleotide that comprises 10 or more contiguous nucleotides selected from a nucleotide sequence of SEQ ID NO: 2;
a second primer set comprising a polynucleotide which comprises 10 or more contiguous nucleotides selected from a nucleotide sequence of SEQ ID NO: 4 and a polynucleotide that comprises 10 or more contiguous nucleotides selected from SEQ ID NO: 5;
a third primer set comprising a polynucleotide which comprises 10 or more contiguous nucleotides selected from a nucleotide sequence of SEQ ID NO: 7 and a polynucleotide that comprises 10 or more contiguous nucleotides selected from SEQ ID NO: 8; and
a fourth primer set comprising a polynucleotide which comprises 10 or more contiguous nucleotides selected from a nucleotide sequence of SEQ ID NO: 10 and a polynucleotide that comprises 10 or more contiguous nucleotides selected from SEQ ID NO: 11;

and (b) at least one vancomycin resistance gene specific primer set selected from the group consisting of
a fifth primer set comprising a polynucleotide which comprises 10 or more contiguous nucleotides selected from a nucleotide sequence of SEQ ID NO: 13 and a polynucleotide that comprises 10 or more contiguous nucleotides selected from a nucleotide sequence of SEQ ID NO: 14;
a sixth primer set comprising a polynucleotide which comprises 10 or more contiguous nucleotides selected from a nucleotide sequence of SEQ ID NO: 16 and a polynucleotide that comprises 10 or more contiguous nucleotides selected from SEQ ID NO: 17;
a seventh primer set comprising a polynucleotide which comprises 10 or more contiguous nucleotides selected from a nucleotide sequence of SEQ ID NO: 19 and a polynucleotide that comprises 10 or more contiguous nucleotides selected from SEQ ID NO: 20; and
an eighth primer set comprising a polynucleotide which comprises 10 or more contiguous nucleotides selected from a nucleotide sequence of SEQ ID NO: 22 and a polynucleotide that comprises 10 or more contiguous nucleotides selected from SEQ ID NO: 23;

wherein the first primer set, second primer set, third primer set, fourth primer set, fifth primer set, sixth primer set, seventh primer set, and eighth primer set hybridize to *Enterococcus faecalis* lactate dehydrogenase gene (ldh), an *Enterococcus faecium* lactate dehydrogenase gene (ldh), an *Enterococcus gallinarum* D-alanine:D-alanine ligase gene2 (ddl2), an *Enterococcus casseliflavus* lactate dehydrogenase gene (ldh), a VanA gene, a VanB gene, a VanC1 gene, and a VanC2/3 gene, respectively;

and wherein (i) the least one *Enterococcus* species specific primer set, the at least one vancomycin resistance gene specific primer set, or both comprise a detectable label; or (ii) the kit further comprises a probe comprising a detectable label for the amplification products of the least one *Enterococcus* species specific primer set and/or a probe comprising a detectable label for the amplification products of the at least one vancomycin resistance gene specific primer set; or both (i) and (ii).

14. The composition of claim 13, further comprising a carrier suitable for PCR.

15. The composition of claim 14, further comprising dNTPs, a buffer, a DNA polymerase, or a combination thereof.

16. The composition of claim 15, further comprising
a target nucleic acid to which the primers of the *Enterococcus* species specific primer set hybridize,
a target nucleic acid to which the primers of the vancomycin resistance gene specific primer set hybridize,
or both.

* * * * *

SEQUENCE LISTING

```
<160> NUMBER OF SEQ ID NOS: 24

<210> SEQ ID NO 1
<211> LENGTH: 20
<212> TYPE: DNA
<213> ORGANISM: Artificial Sequence
<220> FEATURE:
<223> OTHER INFORMATION: Synthetic (Primer: Enterococcus feacalis
      ldh forward)

<400> SEQUENCE: 1
gctgttaaga caactaagtc                                              20

<210> SEQ ID NO 2
<211> LENGTH: 19
<212> TYPE: DNA
<213> ORGANISM: Artificial Sequence
<220> FEATURE:
<223> OTHER INFORMATION: Synthetic (Primer: Enterococcus feacalis
      ldh reverse)

<400> SEQUENCE: 2
ctcacgcatt agcatttac                                               19

<210> SEQ ID NO 3
<211> LENGTH: 19
```

```
<212> TYPE: DNA
<213> ORGANISM: Artificial Sequence
<220> FEATURE:
<223> OTHER INFORMATION: Synthetic (Primer: Enterococcus feacalis
      ldh probe)

<400> SEQUENCE: 3
tcgtcataag tagcagcat                                              19

<210> SEQ ID NO 4
<211> LENGTH: 19
<212> TYPE: DNA
<213> ORGANISM: Artificial Sequence
<220> FEATURE:
<223> OTHER INFORMATION: Synthetic (Primer: Enterococcus feacium
      ldh forward)

<400> SEQUENCE: 4
ttggcattta cttcaccta                                              19

<210> SEQ ID NO 5
<211> LENGTH: 21
<212> TYPE: DNA
<213> ORGANISM: Artificial Sequence
<220> FEATURE:
<223> OTHER INFORMATION: Synthetic (Primer: Enterococcus feacium
      ldh reverse)

<400> SEQUENCE: 5
gctgtaataa caactaagtc a                                           21

<210> SEQ ID NO 6
<211> LENGTH: 17
<212> TYPE: DNA
<213> ORGANISM: Artificial Sequence
<220> FEATURE:
<223> OTHER INFORMATION: Synthetic (Enterococcus feacium ldh probe)

<400> SEQUENCE: 6
ctacttacgc agacgca                                                17

<210> SEQ ID NO 7
<211> LENGTH: 23
<212> TYPE: DNA
<213> ORGANISM: Artificial Sequence
<220> FEATURE:
<223> OTHER INFORMATION: Synthetic (Enterococcus gallinarum ddl2
      forward primer)

<400> SEQUENCE: 7
acaggctttc tttgatattt atg                                         23

<210> SEQ ID NO 8
<211> LENGTH: 18
<212> TYPE: DNA
<213> ORGANISM: Artificial Sequence
<220> FEATURE:
<223> OTHER INFORMATION: Synthetic (Enterococcus gallinarum ddl2
      reverse primer)

<400> SEQUENCE: 8
gccaataaac tgcctttg                                               18

<210> SEQ ID NO 9
<211> LENGTH: 19
<212> TYPE: DNA
<213> ORGANISM: Artificial Sequence
```

```
<220> FEATURE:
<223> OTHER INFORMATION: Synthetic (Enterococcus gallinarum ddl2 probe)

<400> SEQUENCE: 9
ttcgctactc tggttctca                                                        19

<210> SEQ ID NO 10
<211> LENGTH: 18
<212> TYPE: DNA
<213> ORGANISM: Artificial Sequence
<220> FEATURE:
<223> OTHER INFORMATION: Synthetic (Enterococcus casseliflavus ldh
      forward primer)

<400> SEQUENCE: 10
cctacaccat catcgaga                                                         18

<210> SEQ ID NO 11
<211> LENGTH: 20
<212> TYPE: DNA
<213> ORGANISM: Artificial Sequence
<220> FEATURE:
<223> OTHER INFORMATION: Synthetic (Enterococcus casseliflavus ldh
      reverse primer)

<400> SEQUENCE: 11
cagcattttc atcgtctaag                                                       20

<210> SEQ ID NO 12
<211> LENGTH: 17
<212> TYPE: DNA
<213> ORGANISM: Artificial Sequence
<220> FEATURE:
<223> OTHER INFORMATION: Synthetic (Enterococcus casseliflavus ldh
      probe)

<400> SEQUENCE: 12
atccgtgcta aggctac                                                          17

<210> SEQ ID NO 13
<211> LENGTH: 22
<212> TYPE: DNA
<213> ORGANISM: Artificial Sequence
<220> FEATURE:
<223> OTHER INFORMATION: Synthetic (vanA forward primer)

<400> SEQUENCE: 13
ggctcatcct tcggtgtgaa aa                                                    22

<210> SEQ ID NO 14
<211> LENGTH: 23
<212> TYPE: DNA
<213> ORGANISM: Artificial Sequence
<220> FEATURE:
<223> OTHER INFORMATION: Synthetic (vanA reverse primer)

<400> SEQUENCE: 14
cttgccgatt caattgcgta gtc                                                   23

<210> SEQ ID NO 15
<211> LENGTH: 15
<212> TYPE: DNA
<213> ORGANISM: Artificial Sequence
<220> FEATURE:
<223> OTHER INFORMATION: Synthetic (vanA probe)

<400> SEQUENCE: 15
```
tcgtccgcgc tattg                                                    15

<210> SEQ ID NO 16
<211> LENGTH: 18
<212> TYPE: DNA
<213> ORGANISM: Artificial Sequence
<220> FEATURE:
<223> OTHER INFORMATION: Synthetic (vanB forward primer)

<400> SEQUENCE: 16
acgcttacct accctgtc                                                 18

<210> SEQ ID NO 17
<211> LENGTH: 22
<212> TYPE: DNA
<213> ORGANISM: Artificial Sequence
<220> FEATURE:
<223> OTHER INFORMATION: Synthetic (vanB reverse primer)

<400> SEQUENCE: 17
cgtactgttt actttggtta cg                                            22

<210> SEQ ID NO 18
<211> LENGTH: 22
<212> TYPE: DNA
<213> ORGANISM: Artificial Sequence
<220> FEATURE:
<223> OTHER INFORMATION: Synthetic (vanB probe)

<400> SEQUENCE: 18
cggcacggtc aggttcgtcc tt                                            22

<210> SEQ ID NO 19
<211> LENGTH: 25
<212> TYPE: DNA
<213> ORGANISM: Artificial Sequence
<220> FEATURE:
<223> OTHER INFORMATION: Synthetic (vanC1 forward primer)

<400> SEQUENCE: 19
tgcttacggt tctactgtgt tgatc                                         25

<210> SEQ ID NO 20
<211> LENGTH: 22
<212> TYPE: DNA
<213> ORGANISM: Artificial Sequence
<220> FEATURE:
<223> OTHER INFORMATION: Synthetic (vanC1 forward primer)

<400> SEQUENCE: 20
atgccgcagc caatttcaat ac                                            22

<210> SEQ ID NO 21
<211> LENGTH: 16
<212> TYPE: DNA
<213> ORGANISM: Artificial Sequence
<220> FEATURE:
<223> OTHER INFORMATION: Synthetic (vanC1 probe)

<400> SEQUENCE: 21
ccgctatcgc cttttg                                                   16

<210> SEQ ID NO 22
<211> LENGTH: 18
<212> TYPE: DNA

```
<213> ORGANISM: Artificial Sequence
<220> FEATURE:
<223> OTHER INFORMATION: Synthetic (vanC2/3 forward primer)

<400> SEQUENCE: 22
cgcagtgctc ctacaaaa                                              18

<210> SEQ ID NO 23
<211> LENGTH: 18
<212> TYPE: DNA
<213> ORGANISM: Artificial Sequence
<220> FEATURE:
<223> OTHER INFORMATION: Synthetic (vanC2/3 reverse primer)

<400> SEQUENCE: 23
accgacagtc aaagagtc                                              18

<210> SEQ ID NO 24
<211> LENGTH: 23
<212> TYPE: DNA
<213> ORGANISM: Artificial Sequence
<220> FEATURE:
<223> OTHER INFORMATION: Synthetic (vanC2/3 probe)

<400> SEQUENCE: 24
taccgcaacc gatctcaaca ccg                                        23
```